United States Patent [19]
Ellingson et al.

[11] Patent Number: 5,965,111
[45] Date of Patent: *Oct. 12, 1999

[54] FAST DRYING WATER-BORNE NAIL POLISH

[75] Inventors: Peter Christopher Ellingson, Hamilton; Alice Jean Michels, Cincinnati; Edward Dewey Smith, III, Mason, all of Ohio

[73] Assignee: The Procter & Gamble Company, Cincinnati, Ohio

[ * ] Notice: This patent is subject to a terminal disclaimer.

[21] Appl. No.: 09/071,099

[22] Filed: May 1, 1998

[51] Int. Cl.$^6$ .............................. A61K 6/00; A61K 7/00; A61K 7/04
[52] U.S. Cl. ............................ 424/61; 424/401; 427/389
[58] Field of Search ...................... 424/401, 61; 427/389

[56] References Cited

U.S. PATENT DOCUMENTS

| | | | |
|---|---|---|---|
| 4,277,380 | 7/1981 | Williams et al. | 260/18 |
| 4,384,058 | 5/1983 | Galante | 524/32 |
| 4,431,763 | 2/1984 | Reed | 524/389 |
| 4,442,259 | 4/1984 | Isgur et al. | 524/839 |
| 4,766,005 | 8/1988 | Montgomery et al. | 427/4 |
| 4,812,492 | 3/1989 | Eckes et al. | 523/351 |
| 4,844,102 | 7/1989 | Repensek et al. | 132/17 |
| 5,120,529 | 6/1992 | Koch et al. | 424/61 |
| 5,266,322 | 11/1993 | Myers et al. | 424/401 |
| 5,380,520 | 1/1995 | Dobbs | 424/61 |
| 5,538,717 | 7/1996 | La Poterie | 424/61 |
| 5,607,665 | 3/1997 | Calello et al. | 424/61 |
| 5,681,550 | 10/1997 | Rubino | 424/61 |
| 5,716,603 | 2/1998 | Chen et al. | 424/61 |

FOREIGN PATENT DOCUMENTS

| | | |
|---|---|---|
| 87242557 | 8/1987 | Canada . |
| 0 022452 A1 | 1/1981 | European Pat. Off. . |
| 0 061 348 A1 | 9/1982 | European Pat. Off. . |
| 0 063 467 A1 | 10/1982 | European Pat. Off. . |
| 0 325 038 A2 | 7/1989 | European Pat. Off. . |
| 0 418 469 A1 | 3/1991 | European Pat. Off. . |
| 0 455373 A1 | 6/1991 | European Pat. Off. . |
| 0 627212 | 5/1993 | European Pat. Off. . |
| 0 619 111 A1 | 12/1994 | European Pat. Off. . |
| 0299758 B1 | 12/1994 | European Pat. Off. . |
| 0 636 361 | 2/1995 | European Pat. Off. . |
| 0 637600 A1 | 2/1995 | European Pat. Off. . |
| 0 658609 A1 | 6/1995 | European Pat. Off. . |
| 0 679384 | 11/1995 | European Pat. Off. . |
| 0 680742 A1 | 11/1995 | European Pat. Off. . |
| 0 705594 A1 | 4/1996 | European Pat. Off. . |
| 0 797977 A1 | 10/1997 | European Pat. Off. . |
| 57-23632 | 2/1982 | Japan . |
| 4-103512 | 4/1992 | Japan . |
| 4-103513 | 4/1992 | Japan . |
| 4-103514 | 4/1992 | Japan . |
| 5-148122 | 6/1993 | Japan . |
| 5-155737 | 6/1993 | Japan . |
| 5-310531 | 11/1993 | Japan . |
| 7-309721 | 11/1995 | Japan . |
| 9-157135 | 6/1997 | Japan . |
| 9-268113 | 10/1997 | Japan . |
| 883078 | 11/1981 | U.S.S.R. . |
| WO 92/16285 | 3/1992 | WIPO . |
| WO 92/05762 | 4/1992 | WIPO . |
| WO 96/34061 | 10/1996 | WIPO . |
| WO 97/00664 | 1/1997 | WIPO . |
| WO 97/42930 | 11/1997 | WIPO . |

OTHER PUBLICATIONS

U.S. application No. 09/071,424, Ellingson et al., filed May 1, 1998.
U.S. application No. 09/071,098, Ellingson et al., filed May 1, 1998.
U.S. application No. 09/071,097, Smith et al., filed May 1, 1998.
U.S. application No. 09/071,273, Ellingson et al., filed May 1, 1998.
U.S. application No. 09/071,423, Ellingson et al., filed May 1, 1998.
U.S. application No. 09/070,960, Ellingson et al., filed May 1, 1998.

*Primary Examiner*—Thurman K. Page
*Assistant Examiner*—Sharon Howard
*Attorney, Agent, or Firm*—Kelly L. McDow-Dunham; Loretta J. Henderson; David L. Suter

[57] ABSTRACT

The present invention relates to compositions, kits, and films formed therefrom which are useful as cosmetic or therapeutic agents, particularly as polishes for mammalian nails, as well as methods of their use. More particularly, the present invention relates to fast-drying compositions which enhance long wear through their fast-drying properties. When applied to mammalian nails, the present fast-drying compositions exhibit a 5% Diluent Content Time of less than about 38 minutes and or exhibit a 5% Diluent Content Time of less than about 44 minutes and has an Initial Slope greater than about 2.25.

25 Claims, No Drawings

FAST DRYING WATER-BORNE NAIL POLISH

TECHNICAL FIELD

The present invention relates to kits and compositions useful as cosmetic or therapeutic agents and films formed therefrom having defined drying properties. The kits, compositions, and films herein are particularly useful as polishes for mammalian nails.

BACKGROUND OF THE INVENTION

Consumers use nail polishes to cosmetically enhance their nails or protect the nails from everyday conditions and stressors. However, these nail polishes are deficient in many respects, including their inability to provide long wear. Nail polishes which are known or currently available often exhibit deterioration, particularly in the form of chipping or peeling, in as few as one or two days. The occurrence of this deterioration often forces consumers to remove their nail polish soon after original application and reapply additional nail polish to the nails. Consumers may also attempt to correct the unsightly appearance of the deteriorating nail polish by "touching-up" the areas of the nail which exhibit the deterioration, a practice which actually impairs the overall look of the nail polish. Finally, consumers may choose to do nothing about the deterioration and allow, for example, chipping and peeling to progress, resulting in nails which are not only minimally protected from the environment but are unsightly as well.

The art is replete with nail polish compositions which are promoted as having long wear, good adhesion, and/or resistance to chipping. While some nail polish compositions provide better wear than others, a need remains for nail polishes which provide long wear. It would therefore be desirable to provide nail polishes having improved wear properties.

The present inventors have discovered that one property which enhances the wear of a water-borne nail polish is the drying rate which that polish exhibits. Nail polishes delivered from a liquid diluent, such as organic solvent or water, must go through a drying phase which can last from several minutes to many hours. Throughout the duration of this drying phase, the nail polish is particularly susceptible to such damage as scratching, denting, and deterioration. Accordingly, nail polishes which rapidly form dry films will exhibit longer and more beautiful wear.

Several conventional nail polishes are promoted as exhibiting rapid drying rates. However, such polishes typically comprise solvent-borne nitrocellulose which tends to be brittle and inelastic. Such brittleness and inelasticity ultimately lead to chipping and peeling which are hallmarks of poor nail polish wear.

In contrast, known water-borne polishes tend to dry too slowly. To enhance the drying rate of the polishes, formulators often add in drying accelerators at relatively low levels. However, addition of the drying accelerator typically causes instability of the dispersed film-forming polymer, thus "crashing out" the polymer. The present inventors have surprisingly discovered that addition of higher levels of water-miscible organic solvent to a water-borne polymer provides a more stable formulation which provides the desired fast-drying property.

Accordingly, the present inventors have surprisingly discovered water-borne nail polish compositions and kits comprising the compositions which exhibit both rapid drying rates and improved wear at a superior level relative to those presently known and used.

SUMMARY OF THE INVENTION

The present invention relates to fast-drying nail polish compositions which, when applied to mammalian nails, exhibit rapid drying properties. The fast-drying compositions comprise:

(a) a film-forming, water-borne polymer; and
(b) a liquid diluent comprising:
 (i) at least about 20%, by weight of the composition, of a volatile organic solvent; and
 (ii) at least about 4% water;

wherein the composition exhibits a 5% Diluent Content Time of less than about 38 minutes and/or exhibits a 5% Diluent Content Time of less than about 44 minutes and has an Initial Slope greater than about 2.25. The present kits comprise two or more compositions, at least one of which is a fast-drying composition, the fast-drying composition being defined herein. The kits preferably comprise a basecoat composition, a topcoat composition, and, optionally, a midcoat preferably comprise a basecoat composition, a topcoat composition, and, optionally, a midcoat composition. More preferably, the basecoat composition is a fast-drying composition. Each composition comprises a film-forming polymer, a liquid diluent, and, optionally, other components. The present film-forming polymers are selected from polyurethanes, polyacryls, polymethacryls, cellulosic polymers, styrene-acryl copolymers, polystyrene-polyacryl mixtures, polysiloxanes, polyesters, urethane-acryl copolymers, siloxane-urethane copolymers, polyurethane-polymethacryl mixtures, silicone-acryl copolymers, vinyl acetate polymers, and mixtures thereof.

DETAILED DESCRIPTION OF THE INVENTION

The essential components of the present invention are described herein below. Also included are non-limiting descriptions of various optional and preferred components useful in the compositions and kits of the present invention.

The present invention can comprise, consist of, or consist essentially of any of the required or optional components and/or limitations described herein.

All percentages and ratios are calculated by weight unless otherwise indicated. All percentages are calculated based on the total composition unless otherwise indicated.

All component or composition levels are in reference to the active level of that component or composition, and are exclusive of impurities, for example, residual solvents or by-products, which may be present in commercially available sources.

Referred to herein are trade names for materials including, but not limited to, polymers and optional components. The inventors herein do not intend to be limited by materials under a certain trade name. Equivalent materials (e.g., those obtained from a different source under a different name or catalog (reference) number) to those referenced by trade name may be substituted and utilized in the kits, films, and methods herein.

All documents referred to herein, including all patents, patent applications, and printed publications, are hereby incorporated by reference in their entirety.

The compositions, kits, and films of the present invention are suitable for use as a nail polish for mammalian nails. As used herein, the term "suitable for use as a nail polish for mammalian nails" means that the compositions, kits, or films thereof are suitable for use in contact with mammalian nails without undue toxicity, incompatibility, instability, allergic response, and the like.

As used herein, the term "nail polish" is a comprehensive term describing a nail polish composition, product (including coloring products), system, kit, or the like, which is useful for providing, for example, aesthetic, therapeutic, or prophylactic benefits to the nail.

As used herein, the term "mammalian nail" means a keratinaceous plate present at the upper surface of the end of a finger or toe of a primate, most preferably a human, or the homologous claw or hoof of another mammal.

The layers and films herein may be joined to mammalian nails. As used herein, the terms "joined to", "joined to mammalian nails", or the like means in contact with or applied to a mammalian nail through physical forces in such a manner that the layer or film is contiguous to either the nail itself, a preceding layer, a succeeding layer, or matter previously applied to or existing on the nail. The layer or film may be "joined to" a mammalian nail, preceding layer, or succeeding layer even though other matter (such as another preceding or succeeding layer) intervenes. Accordingly, matter which is "joined to", for example, a mammalian nail, need not actually be contiguous to that mammalian nail.

As used herein, the term "contiguous to" means directly joined to by physical forces through touching and boundary sharing with essentially no intervening matter.

As used herein, the term "film" means one or more layers of a nail polish suitable for use on mammalian nails which forms when one or more compositions of the kit is applied to, and dries on, mammalian nails.

As used herein, the term "layer" means one substantially dry coat of nail polish which forms when a composition is applied to, and dries on, a mammalian nail.

As used herein, the term "preceding layer" means a layer which is joined to a nail and is closer in proximity to the nail as compared to a reference layer joined to the same nail. For example, wherein a basecoat and a topcoat are joined to a nail, the basecoat is a preceding layer relative to the topcoat. Similarly, wherein a basecoat, midcoat, and topcoat are joined to a nail, the basecoat and midcoat are preceding layers relative to the topcoat, and the basecoat is a preceding layer relative to both the midcoat and topcoat.

As used herein, the term "succeeding layer" means a layer which is joined to a nail and is further in proximity from the nail as compared to a reference layer joined to the same nail. For example, wherein a basecoat and a topcoat are joined to a nail, the topcoat is a succeeding layer relative to the basecoat. Similarly, wherein a basecoat, midcoat, and topcoat are joined to a nail, the midcoat and topcoat are succeeding layers relative to the basecoat, and the topcoat is a succeeding layer relative to both the basecoat and midcoat.

As used herein, the term "substantially dry" in reference to a film or a layer means that the film or layer feels dry, smooth, or not tacky when it is touched with a human fingertip.

Compositions, Kits, and Films of the Present Invention

The present invention relates to fast-drying nail polish compositions which, when applied to mammalian nails, exhibit rapid drying properties. The present kits comprise two or more compositions wherein at least one of the compositions is a fast-drying composition. The kits preferably comprise a basecoat composition, a topcoat composition, and, optionally, a midcoat composition, wherein the basecoat composition is preferably the fast-drying composition. Each of the present compositions comprises a film-forming polymer, a liquid diluent, and, optionally, one or more other suitable components as described herein. As used herein, the term "film-forming polymer" means a homopolymer, copolymer, or mixture thereof which forms an adherent continuum from a composition when applied to mammalian nails. See. e.g., *Polymer Colloids* Robert M. Fitch, ed., New York: Plenum Press, pp. 173–183 (1971). As used herein, the term "copolymer" includes linear, block, branched, graft, comb, and star copolymers.

Although the term "film-forming polymer" is used herein to describe a polymer in a composition, in some circumstances, polymerization may not actually take place until application of the composition (to the nail, for example) is performed. Accordingly, as used herein, the term "film-forming polymer" is meant to encompass monomers which have not yet polymerized but will upon application to the nail.

The film-forming polymers herein are preferably self-curing polymers. That is, the preferred polymers do not require chemical reaction or introduction of energy (e.g., exposure to ultraviolet rays) to form the adherent continuum.

The film-forming polymers herein can be selected from nonionic, ionic (anionic or cationic), and amphoteric (including zwitterionic) polymers. Wherein the film-forming polymer is water-borne, the polymer is preferably anionic.

The film-forming polymers herein are preferably, but are not limited to, solvent-borne or water-borne polymers. As used herein, the term "water-borne", with reference to a film-forming polymer, means that the polymer was prepared in a mixture comprising water and is preferably added to the composition which it comprises as a mixture (preferably a dispersion) in water. As used herein, the term "solvent-borne", with reference to a film-forming polymer, means that the polymer was prepared under substantially anhydrous conditions and is preferably added to the composition which it comprises as a substantially anhydrous mixture (preferably a solution).

Preferred film-forming polymers of the present invention are selected from polyurethanes, polyacryls, polymethacryls, cellulosic polymers, styrene-acryl copolymers, polystyrene-polyacryl mixtures, polysiloxanes, polyesters, urethane-acryl copolymers, siloxane-urethane copolymers, polyurethane-polymethacryl mixtures, silicone-acryl copolymers, vinyl acetate polymers, and mixtures thereof. The term "polyacryl" includes polyacrylates, polyacrylics, and polyacrylamides. The term "polymethacryl" includes polymethacrylates, polymethacrylics, and polymethacrylamides. The term "cellulosic polymers" includes all cellulose polymers, including esters thereof.

Examples of preferred polyacryls, polymethacryls, and styrene-acryl copolymers include Gelva® 2497 (commercially available from Monsanto Co., St. Louis, Mo.), Duraplus® 2 (commercially available from Rohm & Haas Co., Philadelphia, Pa.), Joncryl® 95 (commercially available from S.C. Johnson Polymer, Sturtevant, Wis.), SCX-1537 (S.C. Johnson Polymer), SCX-1959 (S.C. Johnson Polymer), SCX-1965 (S.C. Johnson Polymer), Joncryl® 530 (S.C. Johnson Polymer), Joncryl® 537 (S.C. Johnson Polymer), Glascol LS20 (commercially available from Allied Colloids, Suffolk, Va.), Glascol C37 (Allied Colloids), Glascol LS26 (Allied Colloids), Glascol LS24 (Allied Colloids), Glascol LE45 (Allied Colloids), Surcol 441® (Allied Colloids), Carboset® CR760 (commercially available from BFGoodrich, Cleveland, Ohio), Carboset® CR761 (BFGoodrich), Carboset® CR763 (BFGoodrich), Carboset® 765 (BFGoodrich), Carboset® 19X2 (BFGoodrich), Carboset® XL28 (BFGoodrich), Hycar 26084 (BFGoodrich), Hycar 26091 (BFGoodrich), Carbobond 26373 (BFGoodrich), Neocryl® A-601 (commercially available from Zeneca Resins, Wilmington, Mass.), Neocryl® A-612 (Zeneca Resins), Neocryl® A-6044 (Zeneca Resins), Neocryl® A-622 (Zeneca Resins), Neocryl® A-623 (Zeneca Resins), Neocryl® A-634 (Zeneca Resins), and Neocryl® A-640 (Zeneca Resins).

An example of a preferred polysiloxane is PSA 590 (commercially available from General Electric, Waterford, N.Y.).

Examples of preferred urethane-acryl copolymers include Sancure® AU-4000 (commercially available from BFGoodrich), Sancure® AU-4010 (BFGoodrich), Witcobond A-100 (commercially available from Witco Performance Chemicals, Houston, Tex.), Witcobond W-610 (Witco Performance Chemicals), NeoPac R-9000 (commercially available from Zeneca Resins), NeoPac R-9030 (Zeneca Resins), and NeoPac R-9699 (Zeneca Resins).

Preferred polyurethanes are selected from aromatic polyether polyurethanes, aliphatic polyether polyurethanes, aromatic polyester polyurethanes, aliphatic polyester polyurethanes, aromatic polycaprolactam polyurethanes, and aliphatic polycaprolactam polyurethanes. The more preferred polyurethanes are selected from aromatic polyether polyurethanes, aliphatic polyether polyurethanes, aromatic polyester polyurethanes, and aliphatic polyester polyurethanes. Examples of preferred polyurethanes include Sancure 2710® and/or Avalure UR 445(which are equivalent copolymers of polypropylene glycol, isophorone diisocyanate, and 2,2-dimethylolpropionic acid, having the International Nomenclature Cosmetic Ingredient name "PPG-17/PPG-34/IPDI/DMPA Copolymer"), Sancure 878®, Sancure 815®, Sancure 1301®, Sancure 2715®, Sancure 1828®, Sancure 2026°0, Sancure 1818®, Sancure 853®, Sancure 830® Sancure 825®, Sancure 776®, Sancure 850®, Sancure 12140®, Sancure 12619®, Sancure 835®, Sancure 843®, Sancure 898®, Sancure 899®, Sancure 1511®, Sancure 1514®, Sancure 1517®, Sancure 1591®, Sancure 2255®, Sancure 2260®, Sancure 2310®, Sancure 2725®, and Sancure 12471® (all of which are commercially available from BFGoodrich, Cleveland, Ohio), Bayhydrol DLN (commercially available from Bayer Corp., McMurray, Pa.), Bayhydrol LS-2033 (Bayer Corp.), Bayhydrol 123 (Bayer Corp.), Bayhydrol PU402A (Bayer Corp.), Bayhydrol 110 (Bayer Corp.), Witcobond W-320 (commercially available from Witco Performance Chemicals), Witcobond W-242 (Witco Performance Chemicals), Witcobond W-160 (Witco Performance Chemicals), Witcobond W-612 (Witco Performance Chemicals), Witcobond W-506 (Witco Performance Chemicals), NeoRez R-940 (commercially available from Zeneca Resins), NeoRez R-960 (Zeneca Resins), NeoRez R-962 (Zeneca Resins), NeoRez R-966 (Zeneca Resins), NeoRez R-967 (Zeneca Resins), NeoRez R-972 (Zeneca Resins), NeoRez R-9409 (Zeneca Resins), NeoRez R-9637 (Zeneca), NeoRez R-9649 (Zeneca Resins), and NeoRez R-9679 (Zeneca Resins).

Preferred solvent-borne polyurethanes include Sanres EX499® (hexylene glycol/neopentyl glycol/isophorone diisocyanate copolymer, Sanres 12711®, Sanres 6010®, and Sanres 6012® (all of which are available from BFGoodrich). The most preferred solvent-borne polyurethane is Sanres EX499®.

Examples of preferred water-borne polyester polyurethanes include Sancure® 2060 and Sancure® 815 (both of which are commercially available from BFGoodrich).

The most preferred water-borne polyurethanes are aliphatic polyether polyurethanes. Examples of preferred aliphatic polyether polyurethanes include Sancure 2710® and/or Avalure UR 445®, Sancure 878®, NeoRez R-966, NeoRez R-967, and Witcobond W-320.

Preferred cellulosic polymers include, for example, nitrocellulose, cellulose acetate butyrate, and cellulose acetate propionate. The most preferred cellulosic polymer is nitrocellulose. Exemplary nitrocellulose polymers are nitrocellulose RS types (nitrogen content of 11.5% to 12.2%), commercially available from Hercules, such as nitrocellulose RS ½ second, nitrocellulose RS ¼ second, nitrocellulose RS ⅛ second, and nitrocelluose RS ¹⁄₁₆ second, and the like. Wherein a composition comprises a cellulosic polymer, the composition preferably comprises a plasticizer.

The compositions of the present invention further comprise a carrier comprising a liquid diluent. The liquid diluent comprises water, organic solvent, or mixtures thereof. Preferred organic solvents include those which are volatile. Preferred volatile organic solvents, at atmospheric pressure, have a boiling point of from about 50° C. to about 140° C., more preferably from about 56° C. to about 125° C., and most preferably from about 56° C. to about 98° C. Wherein the film-forming polymer utilized is water-borne, the organic solvent is preferably water-miscible.

Preferred organic solvents are selected from alcohols, esters, ketones, aromatic hydrocarbons, aliphatic hydrocarbons, ethers, and mixtures thereof. Alcohols and esters are more preferred. Preferred alcohols are monohydric. The most preferred monohydric alcohols are ethanol, iso-propanol, and n-propanol. The most preferred esters are ethyl acetate and butyl acetate. Other non-limiting examples of suitable organic solvents are benzyl alcohol, amyl acetate, propyl acetate, acetone, heptane, iso-butyl acetate, iso-propyl acetate, toluene, methyl acetate, iso-butanol, n-amyl alcohol, n-butyl alcohol, hexane, and methyl ethyl ketone.

The compositions and kits of the present invention may further comprise information which informs a user of the kit or composition, by words, pictures, and/or the like, that use of the kit or composition will provide one or more long wear benefits, including, but not limited to, resistance to chipping, peeling, denting, and/or peeling.

The films herein are formed when a kit of the present invention is applied to mammalian nails. The films of the present invention comprise one or more layers formed from one or more different compositions, most preferably two or three layers formed from two or three different compositions, respectively. The preferred films are those which are comprised of a basecoat and a topcoat, and those which further comprise a midcoat.

The multi-layer films herein form when two or more compositions of the kit, as described herein, are applied to and substantially dry on, mammalian nails. The compositions useful herein may be described as basecoat compositions, midcoat compositions, or topcoat compositions, depending on their intended positioning on the nail.

A. Fast-Drying Compositions

The present invention relates to nail polish compositions which are fast-drying compositions, as defined by their 5%

Diluent Content Time and/or Initial Slope, as defined herein. The present fast-drying compositions are preferably used as basecoat compositions. As used herein, a "basecoat composition" is a composition which is suitable for application to a mammalian nail to form a basecoat, which is a layer of nail polish. A basecoat composition is preferably applied contiguously to a mammalian nail with or without, more preferably with, one or more succeeding layers applied to the resulting basecoat. The basecoat composition is preferably applied contiguously to a mammalian nail with one or more, more preferably one (topcoat), and most preferably two (midcoat and topcoat), succeeding layers joined to the resulting basecoat.

Without intending to be limited by theory, it is believed that the fast-drying compositions of the present invention are beneficial to long wear because they exhibit rapid drying properties. Accordingly, the layers formed from these compositions, as well as the final films (which may include, for example, a midcoat and/or a topcoat) are less susceptible to damage such as, for example, peeling, scratching, denting, and deterioration. Accordingly, the present fast-drying compositions form basecoats and/or other layers and films which exhibit long, beautiful wear.

Without intending to be limited by theory, the present inventors have discovered that the drying rates of the present fast-drying compositions is largely controlled by three variables:

(a) solvent volatility;
(b) percentage of solids in the composition; and
(c) viscosity of the composition.

To increase the drying rate (i.e., increase in the Initial Slope and decrease in the 5% Diluent Content Time), the volatility of the solvent may be increased by increasing the percentage of the organic solvent in the formula and/or substituting higher boiling solvents with lower boiling solvents, and/or the percentage of solids present in the composition may be reduced, and/or the viscosity of the composition may be decreased, e.g., by removing thickeners.

The present fast-drying compositions comprise a film-forming water-borne polymer, a liquid diluent, and, optionally, one or more other suitable components as described herein. The fast-drying compositions preferably comprise from about 0.1% to about 40%, more preferably from about 1% to about 10%, and most preferably from about 2% to about 6% of the film-forming polymer (polymer solids), and at least about 20%, preferably from about 20% to about 90%, more preferably from about 40% to about 90%, even more preferably from about 50% to about 90%, and most preferably from about 70% to about 90% of the volatile organic solvent (as described herein above), by weight of the composition. At least one of the volatile organic solvents utilized should be water-miscible. Preferably, the balance of the fast-drying compositions is substantially water, preferably at least about 4%, more preferably from about 4% to about 85%, still more preferably from about 10% to about 80%, and most preferably from about 25% to about 80%, by weight of the composition, of water.

The film-forming polymers of the fast-drying compositions are preferably water-insoluble at ambient temperature and pressure.

Preferred film-forming polymers for use in the fast-drying compositions are selected from polyurethanes, polyacryls, polymethacryls, urethane-acryl copolymers, styrene-acryl copolymers, cellulosic polymers, polysiloxanes, and mixtures thereof. The more preferred polymers of fast-drying compositions are selected from cellulosic polymers, polyurethanes, polyacryls, polymethacryls, polysiloxanes, and mixtures thereof. Even more preferred polymers of fast-drying compositions are selected from polyurethanes, polyacryls, polymethacryls, urethane-acryl copolymers, styrene-acryl copolymers, and mixtures thereof. The most preferred polymers for use in the fast-drying compositions are polyurethanes. The most preferred polyurethane for use in fast-drying compositions is Sancure 2710® and/or Avalure UR 445®. Preferred types of each of these polymer classes, and examples thereof, are described herein above.

Preferred polyacryls, polymethacryls, and styrene-acryl copolymers for use in the fast-drying compositions are those having a glass transition temperature (Tg) of from about −30° C. to about +60° C., more preferably from about −20° C. to about +20° C., surface energies from about 32 mJ/m$^2$ to about 43 mJ/m$^2$, calculated according to the Harmonic Mean Equation (as determined by the Wilhelmy Technique described by A. W. Neumann and R. J. Good, *Surface and Colloid Science*, Vol. 2, R. J. Good and R. R. Stromberg, Eds., Plenum Press (1979)), and/or polarities from about 0.19 to about 0.29.

The most preferred polyacryls and polymethacryls for use in fast-drying compositions include Glascol LS20, Glascol C37, Joncryl® 95, and SCX-1965.

Wherein the fast-drying composition is used as a basecoat composition, it is preferred to use the fast-drying composition in conjunction with a topcoat composition and/or a midcoat composition, preferably as a kit. Preferred topcoat and midcoat compositions are described herein below.

B. Topcoat Compositions

As used herein, a "topcoat composition" is a composition which is suitable for application to a mammalian nail to form a topcoat, which is a layer of nail polish. The topcoat composition is preferably applied contiguously to, or applied to, one or more preceding layers, one of which is a layer formed from a fast-drying composition of the present invention. The topcoat composition is more preferably applied contiguously to one or two, preferably one (basecoat), and most preferably two (basecoat and midcoat), preceding layers, wherein the basecoat is formed from a fast-drying composition of the present invention.

Without intending to be limited by theory, it is believed that the topcoats further benefit long wear because they deflect environmental stressors by virtue of their hardness, toughness, durability, rigidity, and resistance to chipping.

The present topcoat compositions comprise a film-forming polymer, a liquid diluent, and, optionally, other suitable components as described herein.

The film-forming polymers of the topcoat compositions are preferably either solvent-borne or water-borne and are preferably water-insoluble. Preferred film-forming polymers for topcoat compositions have glass transition temperatures (Tg) from about +20° C. to about +100° C., more preferably from about +30° C. to about +80° C.

The preferred film-forming polymers of topcoat compositions of the present invention are selected from polyurethanes, polyacryls, polymethacryls, styrene-acryl copolymers, cellulosic polymers, polyesters, vinyl acetate polymers, polysiloxanes, polystyrene-polyacryl mixtures, siloxane-urethane copolymers, polyurethane-polymethacryl mixtures, silicone-acryl copolymers, and mixtures thereof. The more preferred film-forming polymers of topcoat compositions are selected from cellulosic polymers, polyurethanes, polyacryls, polymethacryls, polysiloxanes, and mixtures thereof. Even more preferred film-forming polymers of topcoat compositions are selected from polyurethanes, polyacryls, polymethacryls, polystyrene-polyacryl mixtures, styrene-acryl copolymers, siloxane-urethane copolymers, cellulosic polymers, polyesters, polyurethane-polymethacryl mixtures, silicone-acryl copolymers, vinyl acetate polymers, and mixtures thereof. The most preferred film-forming polymers of topcoat compositions are polyacryls and polyurethane-cellulosic polymer mixtures. The most preferred polyacryl for use in topcoat compositions is Duraplus 2®. Preferred types of each of these polymer classes, and examples thereof, are referred to herein above.

Preferred solvent-borne film-forming polymers include polyurethane-polymethacryl mixtures, polyurethane-cellulosic polymer mixtures, polyurethanes, polyacryls, polymethacryls, silicone-acryl copolymers, and mixtures thereof, more preferably, polyacryls and polyurethane-cellulosic polymer mixtures, and most preferably polyacryls.

Wherein the film-forming polymer of the topcoat composition is solvent-borne, the topcoat composition preferably comprises from about 1% to about 50%, more preferably from about 10% to about 25% of the film-forming polymer (polymer solids), by weight of the composition. The topcoat composition comprising the solvent-borne polymer preferably further comprises from about 50% to about 99%, more preferably from about 75% to about 90%, by weight of the composition, of a volatile organic solvent (as described herein above).

Wherein the topcoat composition comprises a solvent-borne film-forming polymer, preferred optional components include thickeners, plasticizers, pigments or dyes, resins, and slip aids.

Preferred water-borne film-forming polymers are selected from polyurethanes, polyacryls, polymethacryls, styrene-acryl copolymers, siloxane-urethane copolymers, and mixtures thereof. More preferred water-borne film-forming polymers are selected from polyacryls and styrene-acryl copolymers and the most preferred water-borne film-forming polymers are polyacryls.

Wherein the film-forming polymer of the topcoat composition is water-borne, the topcoat composition preferably comprises from about 1% to about 40%, more preferably from about 5% to about 30%, and most preferably from about 10% to about 25%, by weight of the composition, of the film-forming polymer (polymer solids).

The topcoat composition comprising the water-borne polymer preferably further comprises a coalescent. Preferably, the topcoat composition comprising the water-borne polymer comprises from about 0.1% to about 30%, more preferably from about 1% to about 20%, by weight of the composition, of a coalescent. Preferably, the ratio of water-borne film-forming polymer to coalescent is from about 1:1 to about 4:1.

Wherein the topcoat composition comprises a water-borne film-forming polymer, other preferred optional components include plasticizers, slip aids (especially waxes and surfactants containing siloxanes), thickeners, and pigments or dyes. Topcoat compositions comprising water-borne film-forming polymers may also optionally contain up to about 50%, more preferably from about 5% to about 40%, and most preferably from about 10% to about 30%, by weight of the composition of a volatile organic solvent. Preferred organic solvents are described herein above.

Wherein the topcoat composition comprises a water-borne polymer, the balance of the composition is substantially water.

The film-forming polymers of the present topcoat compositions may be cross-linked polymers. The present inventors have surprisingly discovered that film-forming polymers which are cross-linked provide properties which are particularly advantageous for topcoat compositions and topcoats including, for example, chip-resistance and superior hardness. Cross-linking may occur either in the composition itself or after application and film formation. However, as used herein, polymers which are not actually cross-linked in the composition but may become cross-linked (i.e., "cross-linkable" polymers) due to the presence of a basic moiety (as described herein) are referred to herein as cross-linked polymers.

As used herein, a "cross-linked polymer" is a polymer which is ionically linked either intramolecularly to itself and/or intermolecularly to one or more other polymers wherein the linkage is formed through an ionic bridge between a metallic ion and a basic moiety comprising the polymer. Cross-linked polymers are preferably intermolecularly linked. Suitable metallic ions include those with an oxidation state of +2, +3, +4 or higher and which are soluble in water. Preferred metallic ions are selected from $Zn^{+2}$, $Mg^{+2}$, $Ca^{+2}$, $Fe^{+2}$, $Fe^{+3}$, $Al^{+3}$, $Mn^{+2}$, $Co^{+2}$, and $Ni^{+2}$. More preferred metallic ions are selected from $Zn^{+2}$, $Mg^{+2}$, $Ca^{+2}$, $Fe^{+2}$, $Fe^{+3}$, and $Al^{+3}$. The most preferred metallic ion is $Zn^{+2}$.

The basic moieties herein are negatively charged or otherwise basic. The basic moieties may be either present in, or pendant from, the film-forming polymer backbone. Preferred basic moieties are selected from carboxylates, sulfonates, sulfates, phosphates, phosphonates, hydroxymates, borate esters, imidazoles, α-thioketones, thioacids, and alkyl amines. More preferred basic moieties are selected from carboxylates, sulfonates, sulfates, phosphates, phosphonates, and alkyl amines. Even more preferred basic moieties are selected from carboxylates, sulfonates, sulfates, phosphates, and phosphonates. The most preferred basic moieties are carboxylates.

The most preferred cross-linkable polymers are selected from polyacryls, polymethacryls, styrene-acryl copolymers, styrene-methacryl copolymers, and mixtures thereof. Cross-linked polymers may be commercially obtained (for example, Duraplus 2®). Cross-linked polymers may alternatively be produced by obtaining or synthesizing a polymer comprising a pendant basic moiety and adding to that polymer a metal ion solution such as, for example, Zinc Oxide Solution #1 (containing about 15% metal ion solids, commercially available from S.C. Johnson & Sons, Inc.) or Bacote 20 (commercially available from Magnesium Elektron, Inc., Flemington, N.J.). Wherein a metal ion solution is added, the solution is added in an amount sufficient to react substantially completely with the available basic moieties present on the film-forming polymer. Preferably, the amount of metal ion solids, relative to the polymer solids present in the composition, is from about 0.2% to about 0.7%, more preferably from about 0.3% to about 0.6%, and most preferably from about 0.4% to about 0.5%, by weight of the composition.

Wherein the film-forming polymer is cross-linked, the polymer is most preferably water-borne.

Wherein a topcoat comprises a cross-linked polymer, the topcoat may be removed from the nail by a wash treatment with a chelator solution which selectively pulls metal cross-linking ions out of the film and destroys the film. Suitable chelator solutions are selected based on the type of metal ion utilized. Exemplary solutions include, for example, aqueous solutions of ethylenediamine disuccinic acid.

C. Midcoat Compositions

As used herein, a "midcoat composition" is a composition which is suitable for application to a mammalian nail to form a midcoat, which is a layer of nail polish. The midcoat composition is preferably applied contiguously to a preceding layer, either a basecoat or another midcoat, most preferably a basecoat, wherein the preceding layer is preferably formed from a fast-drying composition of the present invention. One or more succeeding layers is applied to the layer formed by the midcoat composition. Preferably, a topcoat is applied contiguously to the layer formed by the midcoat composition.

The use of midcoats is preferred wherein there are significant differences between the physical and/or mechanical properties of the basecoat and the topcoat. For example, midcoats preferably relax stress between flexible basecoats and tough topcoats and/or provide color.

The present midcoat compositions comprise a film-forming polymer, a liquid diluent, and, optionally, other suitable components as described herein. Preferred optional components for midcoat compositions are selected from plasticizers, pigments, and dyes.

Midcoat compositions preferably comprise from about 10% to about 25%, more preferably from about 10% to about 18% of a film-forming polymer, from about 60% to about 85%, more preferably from about 60% to about 80% of a volatile organic solvent (as described herein above), and preferably 0% to about 13%, more preferably from about 5% to about 13%, and most preferably from about 6% to about 12% of a plasticizer, by weight of the composition.

Film-forming polymers comprising the midcoat compositions are selected from cellulosic polymers, polyurethanes, polyacryls, polymethacryls, polysiloxanes, and mixtures thereof. More preferred film-forming polymers are polyacryls and cellulosic polymers, with cellulosic polymers being the most preferred. Preferred types of each of these polymer classes, and examples thereof, are described herein above.

Preferred polyacryls for the midcoat compositions are those which are hydrophobic and/or exhibit a glass-transition temperature ($T_g$) of from about −10° C. to about +30° C. Wherein the polyacryl has a Tg higher than about +30° C., the midcoat composition preferably comprises a plasticizer.

Exemplary compositions suitable for use as midcoat compositions are commercially available such as, for example, those marketed under the Max Factor® or Cover Girl® trade names.

Optional Components

The compositions of the present invention may, independently, comprise additional optional components to enhance their performance as a nail polish. For example, antifoams, buffers, chelating agents, coalescents, dispersing agents, dyes, epoxies, fillers, pigments, preservatives, resins, therapeutic and prophylactic agents, thickeners, wax additives, wetting agents, and the like can be included in the compositions herein. Such optional components may be dispersed, solubilized, or otherwise mixed in the carrier and/or the liquid diluent of the compositions. These components may be added to the compositions herein provided they do not substantially hinder the long wear of the films formed from the compositions and kits. Non-limiting examples of optional components are given below.

Coalescents

Coalescents may optionally be added to the compositions to enhance film-formation, most preferably wherein the film-forming polymer is water-borne. Such coalescing aids are known in the art and are typically glycol ethers or glycol ether esters such as $C_{1-10}$ straight or branched chain alkyl glycol alkyl ethers, $C_{1-10}$ straight or branched chain alkyl ether acetates, di-$C_{1-10}$ alkyl ether acetates, and $C_{1-10}$ alkyl glycol phenyl ethers. Preferred coalescing aids include, for example, ethylene glycol ethers (e.g., Dowanol EB®, commercially available from Dow Chemical Co.), diethylene glycol ethers, triethylene glycol ethers, propylene glycol ethers (e.g., Dowanol PnP®, Dow Chemical Co.), dipropylene glycol ethers (e.g., Dowanol DPnP®, Dow Chemical Co.), tripropylene glycol ethers, terpenes, camphor, methyl cellusolve, butyl cellusolve, hexyl cellusolve, methyl carbitol, butyl carbitol, and dibutyl phthalate.

Preferably, a composition comprises from 0% to about 10%, more preferably from about 0. 1% to about 10%, by weight of the composition, of a coalescent.

Pigments or Dyes

Pigments and other suitable coloring agents, such as dyes, may be incorporated into the compositions. Suitable pigments are inorganic or organic pigments known as, for example, the FD&C and D&C colors, lakes, and iron oxides. Such pigments are disclosed in the C.T.F.A. *Cosmetic Ingredient Handbook, First Edition,* 1988. Organic pigments include, for example, D and C Red, Nos. 10, 11, 12, and 13, D and C Red No. 7, D and C Red Nos. 5 and 6, D and C Red Nos. 30 and 34, lacquers such as D and C Yellow No. 5 and D and C Red No. 2, and guanine. Inorganic pigments include, for example, titanium dioxide, bismuth oxychloride, brown iron oxide, and the red iron oxides.

Preferably, the present compositions comprise from 0% to about 5%, more preferably from 0% to about 2%, and most preferably from 0% to about 1%, by weight of the composition, of a pigment or dye.

Plasticizers

Without intending to be limited by theory, plasticizers cause a composition to become more easily deformed. One or more plasticizers may optionally be added to the present compositions. Suitable plasticizers include those disclosed in WO 97/00664, Chen et al, assigned to Eastman Chemical Co. Suitable plasticizers include phthalates, nonionic surfactant polymers, camphor, castor oil, sucrose acetate isobutyrate, alkyl toluenesulfonamides, e.g., ethyl toluenesulfonamide (e.g., Uniplex PX-45, commercially available from Unitex Chemical Corp., Greenboro, N.C.), and polyester acid derivatives (e.g., Uniplex 670P, commercially available from Unitex Chemical Corp.), particularly polyester di- and tri-acids. Preferred plasticizers include diethyl phthalate, dibutyl phthalate, dioctyl phthalate, diethyl tartrate, dibutyl tartrate, diethyl phosphate, dibutyl phosphate, polyester sebacates, such as Paraplex G-25® (commercially available from C.P. Hall, Bedford Park, Ill.) polyester adipates, such as Paraplex G-50® (C.P. Hall) and tetraethylene glycol di-2-ethylhexoate, available as Tegmer® (C.P. Hall). The most preferred plasticizers include dibutyl phthalate, Paraplex G-25®, Paraplex G-50®, camphor, Uniplex PX-45, and Tegmer®.

A composition preferably comprises from 0% to about 15%, more preferably from 0% to about 10%, and most preferably from 0% to about 5%, by weight of the composition, of a plasticizer.

Preservatives

One or more preservatives may optionally be added to the present compositions to prevent, inhibit, or retard microbial growth in the composition. Preferred preservatives include methyl paraben, ethyl paraben, propyl paraben, benzyl alcohol, benzoic acid, benzoates (preferably sodium benzoate), sorbates (preferably potassium sorbate), sodium dehydroacetate, 1-(3-chloroallyl)-3,5,7-triaza-1-azoniaadamantane chloride (which may be obtained commercially as Quatemium-15® from Dow Chemical Co., Midland, Mich.), a mixture of 95% 1,3-dimethylol-5,5-dimethyl hydantoin and 5% 3-iodo-2-propynyl butyl carbamate (which mixture is commercially available as Glydant Plus® from Lonza, Inc., Fair Lawn, N.J.), 1,3-dimethylol-5,5-dimethyl hydantoin (commercially available as Glydant® from Lonza, Inc.), diazolidinyl urea (commercially available as Germall II® from Sutton Laboratories, Chatham, N.J.), imidazolidinyl urea (commercially available as Germall 115® from Sutton Laboratories), phenoxyethanol, and Kathon® (commercially available from Rohm and Haas Co., Philadelphia, Pa.). The most preferred preservatives include methyl paraben, ethyl paraben, propyl paraben, benzyl alcohol, benzoic acid, benzoates (preferably sodium benzoate), sorbates (preferably potassium sorbate), and sodium dehydroacetate.

A composition preferably comprises from 0% to about 10%, more preferably from 0% to about 5%, and most preferably from 0% to about 1%, by weight of the composition, of a preservative.

Resins

Resins including, for example, epoxies and polyacrylics, may optionally be added. Examples of suitable resins include Polytex E75® (commercially available from Estron Chemical, Inc., Calvert City, Kent.) and Acryloid B66® (commercially available from Rohm and Haas, Philadelphia, Pa.).

A composition preferably comprises from 0% to about 15%, more preferably from about 0.5% to about 10%, by weight of the composition, of a resin.

Slip Aids

Slip aids may optionally be added to improve surface friction, water resistance, abrasion resistance, and mechanical properties. Slip aids which may be used include wax additives including, for example, animal, fossil, vegetable, mineral, or synthetic waxes. Preferred wax additives include beeswax, carob, candelilla, ozocerite, polyethylene waxes, paraffin waxes, polypropylene waxes, polytetrafluoroethylene (commercially available as Teflon® from DuPont, Wilmington, Del.), nylons, and polyamides. Specifically, preferred wax additives include, but are not limited to, Jonwax® 26 (commercially available from S.C. Johnson Polymer, Sturtevant, Wis.) Jonwax® 120 (S.C. Johnson Polymer), Chemcor 325N35, Chemcor 43N40, Glaswax® E-1 (commercially available from Allied Colloids, Suffolk, Va.), Glaswax® E-1235 (Allied Colloids), Drewax® E-3030 (commercially available from Ashland Chemical, Boontown, N.J.), Drewax® E-7030 (Ashland Chemical), Lanco® PP1362D (commercially available from Lubrizol, Wichliffe, Ohio), Lanco® A1601 (Lubrizol), and Lanco® TF1780 (Lubrizol).

Other slip aids include materials containing silicone such as copolymers of polyether and polysiloxane. Examples of such slip aids include, for example, Glide 450 and Abil B-8830 (both of which are commercially available from Goldschmidt Chemical, Hopewell, Va.).

The present compositions preferably comprise from 0% to about 10%, more preferably from about 0.1% to about 10%, even more preferably from about 0.5% to about 8%, and most preferably from about 0.5% to about 3% of a slip aid.

Stabilizers

One or more stabilizers may be added to the compositions herein, e.g., to prevent pigment from settling or to achieve desired application properties. Preferably, stabilizers are added to compositions comprising a solvent-borne film-forming polymer. Preferred stabilizers include clays, e.g., organically modified bentonites and hectorites such as stearalkonium bentonite and stearalkonium hectorite (commercially available from Rheox, Inc., Hightstown, N.J.).

Wherein a stabilizer is added, the composition preferably comprises from about 0.25% to about 3%, still more preferably from about 0.25% to about 2.5%, and most preferably from about 1% to about 2% of the stabilizer, by weight of the composition.

Therapeutic and Prophylactic Agents

Therapeutic and/or prophylactic agents such as, for example, vitamins, proteins, anti-fungal and anti-microbial agents, and sunscreens (including UV-A, UV-B, and broad spectrum solar filters) may optionally be added to the present compositions for the further care and protection of the nails.

Thickeners

Thickeners may optionally be added to the compositions and films herein to achieve desired rheology and application properties. Preferably, thickeners are utilized wherein the composition comprises a water-borne film-forming polymer or at least 4% water. Preferred thickeners include hydroxyethyl cellulose, hydroxypropyl cellulose, methyl cellulose, and other conventional cellulosic polymers, associative thickeners (e.g., hydrophobically modified cellulosic polymers, nonionic urethanes, and alkali swellable urethanes) including Aculyn® 44 (commercially available from Rohm & Haas, Philadelphia, Pa.), clays (e.g., laponite and hydrophilic montmorillonite (commercially available as Bentone® from Rheox, Hightstown, N.J.), and natural rubbers and gums (e.g., guar gum, quaternized guar gum sold under the name Jaguar® C-13-S by Rhone-Poulenc, Shelton, Conn.), hydroxypropyl guar gum, gum arabic, carob gum, carrageenan, and xanthan gum).

The present compositions preferably comprise from 0% to about 10%, more preferably from about 0.1% to about 10%, and even more preferably from about 0.1% to about 5% of a thickener, by weight of the composition.

Preferred Kits of the Present Invention

The kits herein are comprised of two or more separate and different compositions, most preferably two or three separate and different compositions. The kits herein are comprised of a fast-drying composition which is preferably a basecoat composition, and preferably, a midcoat composition and/or a topcoat composition. More preferably, the kits are comprised of a fast-drying composition, a topcoat composition, and, optionally, a midcoat composition.

A preferred kit ("Kit 1") having two separate and different compositions comprises a fast-drying composition and a topcoat composition. The fast-drying composition of Kit 1 comprises a film-forming polymer, preferably a water-insoluble polymer, which is selected from polyurethanes, polyacryls, polymethacryls, urethane-acryl copolymers, styrene-acryl copolymers, and mixtures thereof. The topcoat composition of Kit 1 comprises a film-forming polymer, preferably a water-insoluble polymer, which is selected from polyurethanes, polyacryls, polymethacryls, polystyrene-polyacryl mixtures, styrene-acryl copolymers, siloxane-urethane copolymers, cellulosic polymers, polyesters, polyurethane-polymethacryl mixtures, silicone-acryl copolymers, vinyl acetate polymers, and mixtures thereof.

Another preferred kit ("Kit 2") having three separate and different compositions comprises the fast-drying composition and the topcoat composition as described for Kit 1, and further comprises a midcoat composition. The midcoat composition of Kit 2 comprises a film-forming polymer, preferably a water-insoluble polymer, which is selected from cellulosic polymers, polyurethanes, polyacryls, polymethacryls, polysiloxanes, and mixtures thereof.

Another preferred kit ("Kit 3") having two separate and different compositions comprises a fast-drying composition and a topcoat composition. The fast-drying composition of Kit 3 comprises a film-forming polymer, preferably a water-insoluble polymer, which is selected from polyurethanes, polyacryls, polymethacryls, urethane-acryl copolymers, styrene-acryl copolymers, and mixtures thereof. The topcoat composition of Kit 3 comprises a film-forming polymer, preferably a water-insoluble polymer, which is selected from cellulosic polymers, polyurethanes, polyacryls, polymethacryls, polysiloxanes, and mixtures thereof.

Method of Making and Using

The compositions of the present invention are made using conventional formulation and mixing techniques. A layer of nail polish may be prepared by standard application of a composition to mammalian nails using a standard brush-applicator as is commonly utilized in the art and removing sufficient liquid diluent (through evaporation of volatiles, most preferably at ambient pressures and temperatures) to form the substantially dry layer. The multi-layer films of the present invention are prepared in a similar manner by standard application of one or more additional compositions contiguously to the preceding layer. Such application is well-known in art.

The present invention includes a method of coating mammalian nails with a nail polish film, wherein the film comprises one or more layers. The method comprises the steps of:

(i) applying a fast-drying composition contiguously to the nail; and (ii) removing sufficient liquid diluent from the fast-drying composition to form a substantially dry basecoat.

Another method of the present invention further comprises the steps of:

(iii) applying a second composition to the basecoat (which is preferably a midcoat composition or a topcoat composition), wherein the second composition comprises a film-forming polymer and a liquid diluent;

(iv) removing sufficient liquid diluent from the second composition to form a substantially dry layer;

(v) optionally applying a third composition (which is preferably a topcoat composition) to the layer formed from the second composition, wherein the third composition comprises a film-forming polymer and a liquid diluent; and (vi) removing sufficient liquid diluent from the third composition to form a substantially dry layer.

Properties of the Fast-Drying Compositions

The present fast-drying compositions have defined drying properties expressed by a 5% Diluent Content Time and/or an Initial Slope. Drying is a critical process in the setting of any nail polish delivered from a liquid diluent, whether it be organic solvent, water, or blends thereof. It has been discovered that the compositions having the present fast-drying property provide, for example, improved leveling, hardening, and adhesion, relative to the water-borne nail polishes and polishes comprising water which are known in the art. The compositions of the present invention exhibit:

(a) a 5% Diluent Content Time of less than about 38 minutes, more preferably less than about 36 minutes, still more preferably less than about 34 minutes, and most preferably less than about 32 minutes; and/or (b) a 5% Diluent Content Time of less than about 44 minutes and an Initial Slope greater than about 2.25, more preferably greater than about 2.75, and most preferably greater than about 3.00, as defined by the method herein.

The 5% Diluent Content Time quantifies the rate at which a nail polish dries and is determined in the following manner.

Weight as a function of time is measured under controlled conditions as a nail polish dries, forming a film. A Mettler AE 160 balance (commercially available from Mettler-Toledo GmbH, Greifensee, Switzerland) (or equivalent thereof) which has a self-enclosed housing measuring 18.5 centimeters wide by 16 centimeters deep by 23 centimeters high with sliding doors on each side is used to contain a nail polish sample and measure the sample weight. The balance measures weight in grams to 4 decimal places (ten thousandths of a gram). A hole is cut in the lid of the housing concentric to the circular balance plate, through which ⅜ inch diameter Nalgene® tubing (commercially available from Nalge Company, Rochester, N.Y.) (or equivalent thereof) is fed. A nozzle is inserted at the end of the Nalgene® tubing which flares gradually at its outlet end to 8 millimeters inside diameter. The bottom of the nozzle hangs 65 millimeters above the surface of the balance plate by whatever means is convenient to attach it firmly into position. The other end of the Nalgene® tubing is connected to the outflow port of an airflow measuring and metering device, which is connected at its inflow to a dry nitrogen supply tank, which may also contain a pressure regulator. The balance is connected via serial port to a computer which contains software to collect ascii information output from the balance at the start of the experiment and every 60 seconds thereafter. Thus, weight is measured automatically in this set-up. Alternatively, weight can be recorded manually by an operator watching the balance display.

Samples are dried on standard 3 inch long by 1 inch wide microscope slides having a containing ring adhered to one surface. Containing rings are suitably prepared from Bytac Adhesive Teflon® paper (commercially available from DuPont, Wilmington, Del.) (or equivalent thereof). The rings are cut to a specific diameter, namely, ⅞ inch i.d. and a 1 inch o.d., thereby creating a ⅛ inch wide ring with adhesive on one side (e.g., using metal stamps having a ⅞ inch i.d. and a 1 inch i.d.). The ring is adhered to the center of the microscope slide by hand pressure.

To begin measurement of drying rate, all equipment is turned on and airflow is regulated to 1.2 L/min flow rate. To begin a measurement, a microscope slide is prepared with a Teflon® ring, set on the balance, and the balance is zeroed with the slide in position, the airflow on as prescribed, and the balance doors closed. After a zero point is obtained, the slide is removed from the balance and set on a flat surface to receive a sample. 400 μL of the nail polish sample is closed onto the center of the slide using, for example, a micropipette with a combitip. If the sample is low viscosity, it may spontaneously spread to fill the entire container ring area. If the sample does not do so, the tip of the combitip is used to quickly spread the sample evenly to the inside edge of the Teflon® ring. The slide is then quickly set in position on the balance, the door is closed, and the computer is instructed to begin collecting weight information. The elapsed time between dosing the sample onto the microscope slide and starting collection of weight information must be less than 10 seconds. The experiment is continued for five hours, collecting weight information every sixty seconds.

After the data is collected as described above, percent weight loss (PWL) at each time point (each sixty second interval or "time t") is calculated by the following formula:

$$PWL_{timet} = [[(Weight_{time0}) - (Weight_{time1})] \div (Weight_{time0})] * 100\%$$

The percent weight loss values for each time point are plotted versus time. A linear least squares regression to contiguous data points including all six data points collected from t=0 minutes to t=5 minutes, inclusive, is done to determine the Initial Slope (percent weight loss per minute). A steeper slope (larger number) indicates a more rapid drying nail polish in the early stages of drying. To quantify the thoroughness of drying in the later stages of drying, the time point at which 5% residual solvent remains in the nail polish is determined (5% residual solvent content point). This 5% residual solvent content point is defined as the percent total solids level present in the nail polish composition being tested, prior to any drying, (known from composition information or may be derived separately from vacuum oven drying) plus five percent. The 5% residual solvent content point is located on the percent weight loss axis. The 5% Diluent Content Time is the time corresponding to that 5% residual solvent content point and is determined via linear interpolation.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

In the examples herein below, all polymer component percentages are expressed in weight percent of solid polymer (based on the total composition).

Examples 1A–1D

The compositions of Examples 1A–1D are representative of the fast-drying compositions of the present invention and are preferably applied contiguously to the nail as basecoat compositions:

|  | Ex. 1A | Ex. 1B | Ex. 1C | Ex. 1D |
|---|---|---|---|---|
| Sancure 2710 ® | 4% | 5.5% | 5.8% | 5.8% |
| n-Propanol | 71.4% | — | 70% | — |
| Ethyl Acetate | — | 78.1% | — | — |
| iso-Propanol | — | — | — | 32.1% |
| Ethanol | — | 7.9% | — | — |
| Water | 24.4% | 8.5% | 24% | 61.9% |
| Methyl Paraben | 0.1% | — | 0.1% | 0.1% |
| Propyl Paraben | 0.1% | — | 0.1% | 0.1% |

Examples 2A–2E

The compositions of Examples 2A–2E are suitable for use as topcoat compositions and may be applied to the basecoats of the present invention:

|  | Ex. 2A | Ex. 2B | Ex. 2C | Ex. 2D | Ex. 2E |
|---|---|---|---|---|---|
| Duraplus 2 ® | 21% | — | — | 21% | — |
| Nitrocellulose RS¼ second | — | 15% | — | — | 6.75% |
| Sanres ® EX499 | — | 3.6% | — | — | — |
| Sanres ® 12711 | — | 1.5% | 15.5% | — | — |
| Sanres ® 6012 | — | — | — | — | 8.25% |
| Surcol ® 441 | — | — | 4.5% | — | — |
| Dowanol DPnP ® | 10% | — | — | 10% | — |
| Dibutyl Phthalate | 3.9% | — | — | 1.6% | — |
| Glide 450 ® | 0.3% | — | — | 0.3% | — |
| Aculyn 44 ® | 0.5% | — | — | — | — |
| Polytex E-75 (Estron Chemical) | — | 1% | — | — | — |
| Drewax E-3030 ® | — | — | — | 1.2% | — |
| Paraplex G-50 ® | — | 7.6% | — | — | — |
| Butyl Acetate | — | 32.9% | 30% | — | 40% |
| Ethyl Acetate | — | 27.4% | 10% | — | — |
| iso-Propanol | — | 11% | 30% | — | 35% |
| Toluene | — | — | — | — | 10% |
| Acetone | — | — | 10% | — | — |
| Water | 64.3% | — | — | 65.9% | — |

Example 3

The following composition may be used as either a midcoat composition or a topcoat composition.

| Component | Supplier Slurry Code* | Source | Percentage |
|---|---|---|---|
| Solid Nitrocellulose RS ¼ second (available as a slurry) | 50-C3-690 | Akzo Nobel, Somerset, NJ | 7.05% |
| Solid Nitrocellulose RS ½ second (available as a slurry) | 5528 | Scholle Corp., College Park, GA | 7.00% |
| Clay** (available as a slurry) | Bentone slurry | Kirker Enterprises Inc., Paterson, NJ | 1.04% |
| Red #7 Solid (available as a slurry) | Red #7 slurry 6R381 | Penn Color, Doylestown, PA | 0.60% |
| Butyl Acetate |  | J.T. Baker, Phillipsburg, NJ | 27.77% |
| Ethyl Acetate |  | J.T. Baker, Phillipsburg, NJ | 24.00% |
| iso-Propanol |  | J.T. Baker, Phillipsburg, NJ | 6.55% |
| Uniplex 600 |  | Unitex, Greensboro, NC | 11.12% |
| Toluene |  | E.M. Science, Gibbstown, NJ | 6.44% |

-continued

| Component | Supplier Slurry Code* | Source | Percentage |
|---|---|---|---|
| Camphor | | Universal Preservachem, Edison, NJ | 1.43% |
| Dibutyl Phthalate | | Eastman Kodak, Kingsport, TN | 7.00% |
| Total | | | 100% |

*The slurries contain, in addition to the component indicated, other components which are listed in the above formula (such as, for example, butyl acetate and iso-propanol). The percentage given for each component is the percentage of that component only (for example, Solid Nitrocellulose RS ¼ second is present in the control formula at a solids level of 7.05%, exclusive of other components). The levels of the other components in each slurry are combined and reflected in the formula given above. For example, the levels of butyl acetate in Nitrocellulose RS ¼ second slurry, Nitrocellulose RS ½ second slurry, clay, and Red #7 Solid are combined and reflected in the percentage given for the butyl acetate component.
**Clay is 50/50 (weight percent ratio) stearalkonium hectorite/stearalkonium bentonite solids.

The composition of Example 3 may be prepared as follows. Weigh all components together into a sealable jar to hold a 100 gram batch with minimal head-space. Add six stainless steel balls, each of which are 3/16 inches in diameter. Mix on a conventional paint shaker for thirty minutes. Transfer to conventional nail polish bottles.

Example 4

A kit comprising two separate nail polish compositions is prepared. The compositions are a fast-drying basecoat composition of Example 1 and a topcoat composition of Example 2. The basecoat composition is applied contiguously to mammalian nails using a standard brush-applicator. A basecoat is allowed to form. The topcoat composition is applied contiguously to the basecoat using a standard brush-applicator. The topcoat composition is allowed to form a topcoat over a five minute time period, resulting in a film having two layers.

Example 5

A kit comprising two separate nail polish compositions is prepared. The compositions are a fast-drying basecoat composition of Example 1 and a topcoat composition which is a conventional nail polish such as Max Factor® International (comprising butyl acetate, ethyl acetate, nitrocellulose, toluenesulphonamide formaldehyde resin, dibutyl phthalate, toluene, iso-propanol, camphor, benzophenone, stearalkonium hectorite, and polyester resin). The basecoat composition is applied contiguously to mammalian nails using a standard brush-applicator. A basecoat is allowed to form. The topcoat composition is applied contiguously to the basecoat using a standard brush-applicator. The topcoat composition is allowed to form a topcoat over a five minute time period, resulting in a film having two layers.

Example 6

A kit comprising three separate nail polish compositions is prepared. The compositions are a fast-drying basecoat composition of Example 1, a midcoat composition which is a conventional nail polish, such as Max Factor® International (comprising butyl acetate, ethyl acetate, nitrocellulose, toluenesulphonamide formaldehyde resin, dibutyl phthalate, toluene, iso-propanol, camphor, benzophenone, stearalkonium hectorite, and polyester resin) and a topcoat composition of Example 2. The basecoat composition is applied contiguously to mammalian nails using a standard brush-applicator. A basecoat is allowed to form. The midcoat composition is applied contiguously to the basecoat using a standard brush-applicator. The midcoat composition is allowed to form a layer over a period of five minutes, resulting in a film having two layers. The topcoat composition is applied contiguously to the layer formed from the midcoat composition using a standard brush-applicator. The topcoat composition is allowed to form a topcoat over a period of five minutes, providing a film having three layers.

Example 7

A kit comprising two separate nail polish compositions is prepared. The compositions are a fast-drying basecoat composition of Example 1 and the topcoat composition as set forth in Example 3. The basecoat composition is applied contiguously to mammalian nails using a standard brush-applicator. A basecoat is allowed to form. The topcoat composition is applied contiguously to the basecoat using a standard brush-applicator. The topcoat composition is allowed to form a topcoat over a five minute time period, resulting in a film having two layers.

What is claimed is:

1. A fast-drying composition suitable for use as a nail polish for mammalian nails comprising:
   (a) a film-forming, water-borne polymer; and
   (b) a liquid diluent comprising:
      (i) at least about 20%, by weight of the composition, of a volatile organic solvent; and
      (ii) at least about 4% water;
wherein the composition exhibits a 5% Diluent Content Time of less than about 38 minutes.

2. A composition according to claim 1 wherein the polymer is a water-insoluble polymer selected from the group consisting of polyurethanes, polyacryls, polymethacryls, urethane-acryl copolymers, styrene-acryl copolymers, and mixtures thereof.

3. A composition according to claim 2 wherein the polymer is a polyurethane.

4. A composition according to claim 1 exhibiting a 5% Diluent Content Time of less than about 36 minutes.

5. A composition according to claim 1 exhibiting a 5% Diluent Content Time of less than about 34 minutes.

6. A composition according to claim 1 exhibiting a 5% Diluent Content Time of less than about 32 minutes.

7. A composition suitable for use as a nail polish for mammalian nails comprising:
   (a) a film-forming, water-borne polymer; and
   (b) a liquid diluent comprising:
      (i) at least about 20%, by weight of the composition, of a volatile organic solvent; and
      (ii) at least about 4% water;
wherein the composition exhibits a 5% Diluent Content Time of less than about 44 minutes and an Initial Slope greater than about 2.25.

8. A composition according to claim 7 wherein the polymer is a water-insoluble polymer selected from the group consisting of polyurethanes, polyacryls, polymethacryls, urethane-acryl copolymers, styrene-acryl copolymers, and mixtures thereof.

9. A composition according to claim 8 wherein the polymer is a polyurethane.

10. A composition according to claim 7 exhibiting an Initial Slope of greater than about 2.75.

11. A composition according to claim 7 exhibiting an Initial Slope of greater than about 3.00.

12. A kit suitable for use as a nail polish for mammalian nails, the kit comprising two or more different compositions wherein each composition comprises a film-forming polymer and a liquid diluent, wherein at least one of the compositions is a composition according to claim 1.

13. A kit according to claim 12 wherein the water-borne polymer is a water-insoluble polymer selected from the group consisting of polyurethanes, polyacryls, polymethacryls, urethane-acryl copolymers, styrene-acryl copolymers, and mixtures thereof.

14. A kit according to claim 13 wherein the water-borne polymer is a polyurethane.

15. A kit according to claim 12 comprising a fast-drying composition and a topcoat composition wherein:
  (a) wherein the water-borne polymer of the fast-drying composition is selected from the group consisting of polyurethanes, polyacryls, polymethacryls, urethane-acryl copolymers, styrene-acryl copolymers, and mixtures thereof; and
  (b) the topcoat composition comprises a film-forming water-insoluble polymer selected from the group consisting of polyurethanes, polyacryls, polymethacryls, polystyrene-polyacryl mixtures, styrene-acryl copolymers, siloxane-urethane copolymers, cellulosic polymers, polyesters, polyurethane-polymethacryl mixtures, silicone-acryl copolymers, vinyl acetate polymers, and mixtures thereof.

16. A kit according to claim 12 comprising a basecoat composition and a topcoat composition wherein:
  (a) wherein the water-borne polymer of the fast-drying composition is selected from the group consisting of polyurethanes, polyacryls, polymethacryls, urethane-acryl copolymers, styrene-acryl copolymers, and mixtures thereof; and
  (b) the topcoat composition comprises a film-forming water-insoluble polymer selected from the group consisting of cellulosic polymers, polyurethanes, polyacryls, polymethacryls, polysiloxanes, and mixtures thereof.

17. A kit according to claim 15 further comprising a midcoat composition comprising a film-forming water-insoluble polymer selected from the group consisting of cellulosic polymers, polyurethanes, polyacryls, polymethacryls, polysiloxanes, and mixtures thereof.

18. A kit according to claim 12 wherein the 5% Diluent Content Time is less than about 36 minutes.

19. A kit according to claim 12 wherein the 5% Diluent Content Time is less than about 34 minutes.

20. A kit according to claim 12 wherein the 5% Diluent Content Time is less than about 32 minutes.

21. A kit suitable for use as a nail polish for mammalian nails, the kit comprising two or more different compositions wherein each composition comprises a film-forming polymer and a liquid diluent, wherein at least one of the compositions is a composition according to claim 7.

22. A kit according to claim 21 wherein the Initial Slope is greater than about 2.75.

23. A kit according to claim 21 wherein the Initial Slope is greater than about 3.00.

24. A method of coating mammalian nails with a nail polish film, wherein the method comprises the steps of:
  (i) applying a composition according to claim I contiguously to the nail; and
  (ii) removing sufficient liquid diluent from the composition to form a substantially dry layer.

25. A method according to claim 24 further comprising the steps of:
  (iii) applying a second composition to the nail, wherein the second composition comprises a film-forming polymer and a liquid diluent;
  (iv) removing sufficient liquid diluent from the second composition to form a substantially dry layer;
  (v) optionally applying a third composition to the nail, wherein the third composition comprises a film-forming polymer and a liquid diluent; and
  (vi) removing sufficient liquid diluent from the third composition to form a substantially dry layer.

* * * * *